United States Patent [19]
Stein et al.

[11] 4,029,884
[45] June 14, 1977

[54] ADENOSINE-5'-CARBOXYLIC ACID AMIDES

[75] Inventors: Herman Hal Stein, Skokie, Ill.; Raj Nandan Prasad, Pierrefonds, Canada

[73] Assignee: Abbott Laboratories, North Chicago, Ill.

[22] Filed: Mar. 22, 1972

[21] Appl. No.: 236,980

Related U.S. Application Data

[63] Continuation-in-part of Ser. No. 125,893, March 18, 1971.

[52] U.S. Cl. .................. 536/26; 424/180; 536/24
[51] Int. Cl.² ...................... C07H 19/18
[58] Field of Search .................... 536/26

[56] References Cited
UNITED STATES PATENTS

| | | | |
|---|---|---|---|
| 3,830,796 | 8/1974 | Prasad et al. | 536/26 |
| 3,855,206 | 12/1974 | Prasad et al. | 536/26 |

*Primary Examiner*—Johnnie R. Brown
*Attorney, Agent, or Firm*—Vincent A. Mallare; Robert L. Niblack

[57] ABSTRACT

Adenosine-5'-carboxylic acid amides represented by the formula

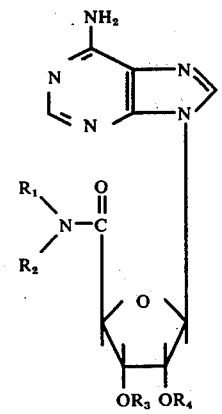

wherein $R_1$ and $R_2$ are each selected from the group consisting of hydrogen, loweralkyl, lowerhaloalkyl, lowerhydroxyalkyl, lowercycloalkyl, loweralkylcycloalkyl, loweralkenyl, lowerhaloalkenyl, lowerhydroxyalkenyl, loweralkynyl, lowerhaloalkynyl, benzylamino, phenyl, loweralkylphenyl, loweralkoxyloweralkyl, substituted phenyl, 2-methylfuran or di($C_1$-$C_4$)alkylamino($C_1$-$C_4$)alkyl, adamantyl or $R_1$ and $R_2$ taken together form a 5 or 6 membered heterocyclic moiety; $R_3$ and $R_4$ are hydrogen or acyl, or taken together form an isopropylidene or a benzylidene group; or a pharmaceutically acceptable acid addition salt thereof.

17 Claims, No Drawings

ADENOSINE-5'-CARBOXYLIC ACID AMIDES

CROSS-REFERENCE TO RELATED APPLICATION

This application is a continuation-in-part of copending application Ser. No. 125,893 filed Mar. 18, 1971.

DETAILED DESCRIPTION OF THE INVENTION

This invention relates to adenosine derivatives and more particularly relates to adenosine-5'-carboxylic acid amides, to intermediates useful in their preparation and to methods of using the compounds.

The compounds of this invention are represented by the formula

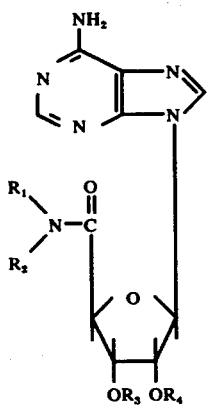

wherein $R_1$ and $R_2$ are each selected from the group consisting of hydrogen, loweralkyl, lowerhaloalkyl, lowerhydroxyalkyl, lowercycloalkyl, loweralkylcycloalkyl, loweralkenyl, lowerhaloalkenyl, lowerhydroxyalkenyl, loweralkynyl, lowerhaloalkynyl, benzylamino, phenyl, loweralkylphenyl, loweralkoxyloweralkyl, substituted phenyl, 2-methylfuran or di($C_1$-$C_4$-)alkylamino($C_1$-$C_4$)alkyl, adamantyl or $R_1$ and $R_2$ taken together form a 5 or 6 membered heterocyclic moiety; $R_3$ and $R_4$ are hydrogen or acyl, or taken together form an isopropylidene or a benzylidene group; or a pharmaceutically acceptable acid addition salt thereof. Compounds wherein $R_3$ and $R_4$ are hydrogen are useful in treating cardiovascular disorders and are particularly useful as anti-hypertensive and anti-anginal agents. A number of amides also exhibit anti-inflammatory activity.

The term "loweralkyl" as used herein refers to $C_1$-$C_6$ straight and branched chain alkyl groups including methyl, ethyl, n-propyl, iso-propyl, n-butyl, sec-butyl, tert-butyl, iso-butyl, n-pentyl, iso-pentyl, neo-pentyl, n-hexyl, iso-hexyl and the like.

The term "loweralkenyl" refers to alkenyl groups having from 2-6 carbon atoms such as vinyl, allyl, methallyl, 1-pentenyl and the like.

The term "loweralkynyl" refers to $C_2$-$C_6$ alkynyl groups including ethynyl, propargyl, 2-butynyl, 1-pentynyl and 2-hexynyl.

The term "halo" includes chloro, fluoro, bromo and iodo.

The term "lowercycloalkyl" refers to $C_3$-$C_7$ cycloalkyl groups and includes cyclopropyl, cyclobutyl, cyclopentyl, cyclohexyl and cycloheptyl.

The term "loweralkylcycloalkyl" refers to $C_3$-$C_7$ cycloalkylloweralkyl groups such as cyclopropylmethyl and the like.

The term "alkoxyloweralkyl" refers to alkoxyalkyl groups having a total of no more than 6 carbon atoms such as methoxymethyl, methoxyethyl, ethoxyethyl, propoxypropyl, propoxyethyl and the like.

The term "substituted phenyl" refers to a phenyl group substituted in the ortho, meta or para position by a loweralkyl, loweralkoxy or halo atom or a disubstituted phenyl group containing two of the above mentioned radicals such as 3,4-dimethoxyphenyl, 3,5-dimethylphenyl, 3-chloro-4-methylphenyl and the like.

The term "5 or 6 membered heterocyclic moiety" includes morpholino, thiomorpholino, piperidino, homopiperidino, piperazino, pyrrolidino and the like.

The term "pharmaceutically acceptable acid addition salts" refers to salts prepared by reacting the amide with an organic or inorganic acid. Representative salts include hydrochloride, hydrobromide, sulfate, bisulfate, acetate, valerate, oleate, laurate, borate, benzoate, lactate, phosphate, tosylate, citrate, maleate, succinate, tartrate, napsylate and the like.

Representative compounds of this invention include: adenosine-5'-carboxamide; adenosine-5'-(N-methyl)-carboxamide; adenosine-5'-(N-iso-propyl)carboxamide; adenosine-5'-(N-ethyl)-carboxamide; adenosine-5'-(N-n-propyl)carboxamide; adenosine-5'-(N-iso-butyl)carboxamide; adenosine-5'-(N-n-butyl)carboxamide; adenosine-5'-(N-n-pentyl)carboxamide; adenosine-5'-(N-iso-pentyl)carboxamide; adenosine-5'-(N,N-dimethyl)carboxamide; adenosine-5'-(N,N-diethyl)carboxamide; adenosine-5'-(N,N-diisopropyl)carboxamide; adenosine-5'-(N-methyl-N-ethyl)carboxamide; adenosine-5'-(N-cyclobutyl)carboxamide; adenosine-5'-(N-cyclopropylmethyl)carboxamide; adenosine-5'-(N-propargyl)-carboxamide; adenosine-5'-(N-allyl)carboxamide; adenosine-5'-(N-ethoxyethyl)carboxamide; adenosine-5'-(N,N-dicyclopropylmethyl)carboxamide; adenosine-5'-(N,N-dichloroethyl)carboxamide.

The compounds of this invention are useful as blood pressure lowering agents when administered to hypertensive patients in dosages of from 0.001–25 mg./kg. of body weight daily. The compounds are also useful in the management and treatment of angina pectoris when administered to patients suffering from or prone to such attacks in dosages of from 0.001–25 mg./kg. of body weight daily. In both instances, it is preferred to administer the compounds orally, however, the compounds may also be administered via intravenous administration. The compounds can be administered in single doses, however, it is preferred that they can be administered in divided doses, i.e., 3–4 times daily.

In addition to their cardiovascular activity, a number of amides exhibit anti-inflammatory activity at dosages of 0.04 to 100 mg./kg. of body weight, with a number of the compounds having an $ED_{25}$ in the rat paw edema test of under 1 mg./kg.

The compounds of this invention can be prepared by converting adenosine-5'-carboxylic acid (prepared from 2',3'-isopropylidene adenosine according to the method described by Harmon et al, Chem. Ind. 1969, 1141 to the corresponding acid chloride by reacting it with thionyl chloride and then reacting the acid chloride with ammonia or an appropriately substituted alkyl amine such as methylamine, dimethylamine and the like. It will be obvious to those skilled in the art that other well-known procedures can also be employed to prepare the compounds of this invention.

The 2',3'-hydroxyl groups of the starting acid can be temporarily blocked by using the protective groups which are conventional in sugar chemistry. The protecting groups can be acyl groups, preferably acetyl or benzoyl groups, or ketals, such as the 2',3'-isopropylidene or benzylidene, which can be converted back to the 2',3'-dihydroxy compounds by methods well-known in the art, preferably after the conversion of the acid chloride to the amide. The 2',3'-isopropylidene adenosine starting material is commercially available from Pfanstiehl Corporation, North Chicago, Illinois and the preparation thereof is well known. A number of the intermediates also exhibit cardiovascular activity.

The preferred synthetic route is represented by the following reaction scheme:

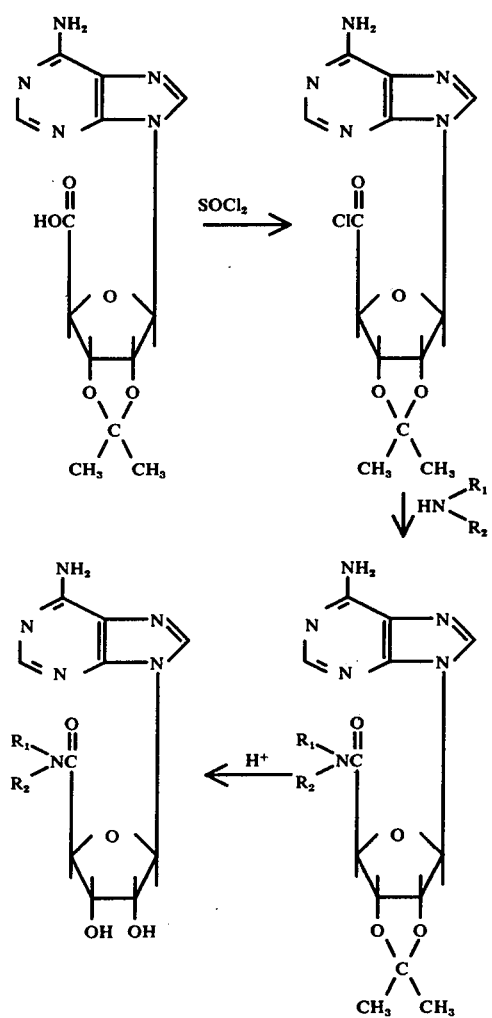

The following examples further illustrate the present invention:

EXAMPLE 1

2',3'-Isopropylidene Adenosine-5'-Carboxylic Acid Chloride

2',3'-Isopropylidene adenosine-5'-carboxylic acid (12.8 g.) [prepared according to the method of R. E. Harmon, et al, Chem. Ind. London, No. 33, 1141 (1969)] was added to an excess of thionyl chloride (70 ml.) at 0° C. The mixture was stirred for 1 hour at 0° C. and then the temperature was allowed to go up to room temperature for another hour. The clear solution was poured, in a thin stream, onto a large volume of well stirred dry ether. The yellow precipitate of 2',3'-isopropylidene adenosine-5'-carboxylic acid chloride, m.p. 190°–195° dec. was filtered and washed with an excess of dry ether. This material was used directly for the preparation of the amides without any further purification.

EXAMPLE 2

Adenosine-5'-Carboxamide

A mixture of 6.8 g. of 2',3'-isopropylidene adenosine-5'-carboxylic acid chloride and 50 ml. of liquid anhydrous ammonia was stirred for two (2) hours at −60° to −50° C. At the end of this time the ammonia was allowed to evaporate off at room temperature. The residue was triturated with cold aqueous sodium bicarbonate solution (1N). The resulting insoluble solid was filtered, washed with cold water and recrystallized from ethanol to yield 3.5 g. (55%) of crude 2',3'-isopropylidene adenosine-5'-carboxamide, m.p. 220°–222°. The amide was then mixed with 100 ml. of 1 N hydrochloric acid and maintained at a temperature of between 60°–70° for 45 minutes. The acidic solution was then cooled, neutralized with sodium bicarbonate and the mixture evaporated to dryness under reduced pressure.

The residue was recrystallized three times from absolute ethanol to yield one gram of pure adenosine-5'-carboxamide, m.p. 245°–246°; $[\alpha]_D^{27}$ −29°±0.9° (c, 1.08 in 1N HCl). Elemental analysis and nuclear magnetic resonance data confirmed the identity of the compound.

EXAMPLE 3

Adenosine-5'-(N-methyl)Carboxamide

2',3'-Isopropylidene adenosine-5'-[N-methylcarboxamide] (m.p. 264°–265°) was prepared according to the method of Example 2 from 2',3'-isopropylidene adenosine-5'-carboxylic acid chloride and an excess of dry liquid methylamine at −20° to −10° C. The 2',3'-isopropylidene group was cleaved by the use of 1N HCl at 60° for 45 minutes to give adenosine-5'-(N-methyl)-carboxamide in 44% yield; m.p. 240–241°; $[\alpha]_D^{27}$ −23° ± 0.6° (c, 3.2 in 1N HCl). Elemental analysis and nuclear magnetic resonance data confirmed the identity of the compound.

EXAMPLE 4

Adenosine-5'-(N,N-dimethyl)carboxamide 13.5 g. of 2',3'-isopropylidene adenosine-5'-carboxylic acid chloride was stirred with excess dry dimethylamine at −10° to 0° C. The clear solution was allowed to warm to room temperature. In about 3 hours the unreacted dimethylamine had evaporated off. The residue was washed with ether and dissolved in the minimum amount of cold aqueous NaHCO₃ solution (1N). The basic aqueous solution so obtained was extracted five times with 50 ml. of chloroform. The chloroform extract was dried and evaporated under reduced pressure to give an amorphous solid. This solid was dissolved in dilute acetic acid, filtered (to remove a small amount of insoluble material) and the filtrate was extracted four times with 50 ml. of chloroform. The chloroform extract was dried and evaporated to dryness under reduced pressure to yield 6.0 g. (43%) of 2',3'-isopropylidene adenosine-5'-(N,N-dimethyl)carboxamide. The crude amide (m.p. 106°–110°) was dissolved in 100 ml. of 1N HCL and kept at 60°–70° for 45 minutes. The solution was then cooled, basified with NaHCO₃ and evaporated to dryness under reduced pressure.

The residue, upon recrystallization three times from absolute ethanol, gave 3.0 g. (23%) of adenosine-5'-(N,N-dimethyl)carboxamide as a monohydrate; m.p. 190°–191°; $[\alpha]_D^{27}$ − 17° ± 0.3° (c, 3 in 1N HCl). Elemental analysis and nuclear magnetic resonance data confirmed the identity of the compound.

EXAMPLE 5

Adenosine-5'-[(N-ethyl)-Carboxamide]

Freshly prepared 2',3'-isopropylidene adenosine-5'-carboxylic acid chloride (prepared from 6.4 g. of 2',3'-isopropylidene-5'-carboxylic acid) was stirred with excess of dry liquid ethyl amine at −50° to −35°. The clear red-orange solution was allowed to warm up to room temperature and kept at this temperature for 15 hours. At the end of this period the excess of ethyl amine had evaporated off. The residue was triturated with cold aqueous NaHCO₃ solution. The white precipitate was filtered off and washed with a small amount of cold water to yield 3.1 g. (44.5%) of crude 2',3'-isopropylidene-5'-[(N-ethyl)-carboxamide] m.p. 225°–227°. $R_f$: 0.72 (silica gel) system: n.BuOH:-H₂O:NH₄OH (86:14:5). The above amide was mixed with 80 ml. of 1 N HCl and kept at 65° for 45 minutes. The acidic solution was then cooled and basified with NaHCO₃. The mixture was then evaporated to dryness under reduced pressure, and the residue recrystallized twice from absolute ethanol and finally from water. The white crystalline product was dried in vacuo for 2 days over P₂O₅ at 70°–78° to give 0.9 g. (32%) of adenosine-5'-[(N-ethyl)carboxamide] which melted slowly at 136°–172° and solidified again at 148°–150° and finally melted at 246°–247° (sharp). $[\alpha]_D^{26}$ −163 (c, 0.92 in 1 N HCl); $R_f$: 0.51 (silica gel). System: n-BuOH:H₂O:NH₄OH (86:14:05); NMR (deuterated DMSO) peaks (in ppm) at 5.6 (2'-OH, 3'-OH), 7.4 (6C-NH₂); 8.8 (CONH); 3.2 (CH₂CH₃). Elemental analysis and NMR data confirmed the identity of the compound.

The following compounds are prepared according to the method of Example 4, substituting the appropriate amine for diethylamine.

| Example | R₁ | R₂ | Mp° C. | Recrystin. Solvent | $[\alpha]_D^{26}$ Rotation | C/1NHCl | $R_f$ |
|---|---|---|---|---|---|---|---|
| 6 | —C₂H₅ | H | 246–247 | H₂O | −16.3±0.54° | 0.92 | 0.51 |
| 7 | —C₂H₄-O—C₂H₅ | H | 107–110 | EtOH | −7.4±0.9° | 0.54 | 0.44 |
| 8 | —CH(CH₃)(CH₃) | H | 137–141 | EtOH | −9±2.2° | 0.223 | 0.53 |
| 9 | —(CH₂)₃CH₃ | H | 104–106 | DMF | −8.9±1.5° | 0.334 | 0.56 |
| 10 | —CH₂—CH=CH₂ | H | 223–224 | EtOH | −13.5±1.4° | 0.369 | 0.50 |
| 11 | —CH₂—C≡CH | H | 135–137 | EtOH | −27.5±0.5° | 0.44 | 0.44 |
| 12 | ◁ | H | 249–250 | EtOH | −6.8±0.8° | 0.584 | 0.47 |
| 13 | —CH₂—⟨phenyl⟩ | H | 130–133 | H₂O | −6.3±1.5° | 0.315 | 0.55 |
| 14 | —(CH₂)₃CH₃ | H | 125 | MeOH-Acetone | | | |
| 15 | —(CH₂)₂CH₃ | H | 220–222 | MeOH-Acetone-Ether | | | |
| 16 | —CH(CH₂CH₃)(CH₂CH₃) | H | a | MeOH-EtOEt | −1.6±0.8° | 0.63 | |
| 17 | —CH₂COOC₂H₅ | H | 165–170 | Acetone-Ether | −3.7±0.23° | 2.16 | | a no sharp melting point
b TLC was done on Eastman 6060 Silica Gel Chromagram Sheet with Fluorescent indicator.

Solvent System used was: n-BuOH:NH₄OH:H₂O=86:5:14

-continued

ANALYSES

| Example Contd. | Empirical Formula | Calculated C | H | N | O | Found C | H | N | O |
|---|---|---|---|---|---|---|---|---|---|
| 6 | $C_{12}H_{16}N_6O_4 \cdot \frac{1}{2}H_2O$ | 45.42 | 5.40 | 26.48 | 22.68 | 45.76 | 5.87 | 25.51 | 22.48 |
| 7 | $C_{14}H_{20}N_6O_5$ | 47.73 | 5.72 | 23.85 | 22.70 | 47.49 | 5.85 | 24.05 | 23.01 |
| 8 | $C_{13}H_{18}N_6O_4$ | 48.49 | 5.62 | 26.05 | 19.83 | 48.28 | 5.78 | 26.25 | 20.21 |
| 9 | $C_{16}H_{24}N_6O_4 \cdot \frac{1}{2}H_2O$ | 51.47 | 6.75 | 22.51 | 19.28 | 51.52 | 6.69 | 22.41 | 19.13 |
| 10 | $C_{13}H_{18}N_6O_4 \cdot H_2O$ | 46.20 | 5.36 | 24.82 | 23.62 | 46.28 | 5.58 | 24.90 | 24.00 |
| 11 | $C_{13}H_{14}N_6O_4$ | 49.10 | 4.43 | 26.38 | 20.09 | 49.15 | 4.60 | 26.59 | 20.48 |
| 12 | $C_{13}H_{18}N_6O_4$ | 48.79 | 5.83 | 26.22 | 19.96 | 48.98 | 5.52 | 25.81 | 19.41 |
| 13 | $C_{12}H_{18}N_6O_4$ | 55.13 | 4.90 | 22.69 | 17.28 | 54.83 | 5.00 | 22.91 | 17.71 |
| 14 | $C_{14}H_{20}N_6O_4$ | 49.98 | 5.99 | 24.98 | 19.02 | 50.12 | 6.06 | 25.14 | 19.35 |
| 15 | $C_{13}H_{18}N_6O_4 \cdot CH_3OH$ | 47.44 | 6.25 | 23.71 | 22.57 | 47.00 | 5.80 | 24.86 | 22.69 |
| 16 | $C_{15}H_{22}N_6O_4$ | 51.41 | 6.33 | 23.98 | 18.26 | 50.39 | 6.36 | 23.55 | 17.36 |
| 17 | $C_{15}H_{20}N_6O_4$ | 51.71 | 5.78 | 24.12 | 18.37 | 51.51 | 6.06 | 24.17 | 18.75 |

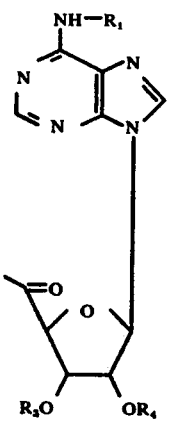

| Example | $R_1$ | $R_2$ | $R_3$ | $R_4$ | MP° C | $[\alpha]_D^{26°}$ Rotation | c | Solvent |
|---|---|---|---|---|---|---|---|---|
| 18 | H | 2,3-dimethylphenyl | H | H | 203 | +14.8° ± 2° | 1.7 | 1N.HCl |
| 19 | H | cyclohexyl | H | H | 175–79 | −3.3° ± 1° | 1.5 | $CH_3COOH$ |
| 20 | H | $C_6H_5CH_2NH-$ | H | H | 245–47 | −18° ± 2° | 0.223 | 1N.HCl |
| 21 | H | $HOCH_2CH_2-$ | H | H | 196–98 | −28.8° ± 1° | 1.6 | 1N.HCl |
| 22 | H | $C_6H_5OCH_2CH_2-$ | H | H | 125–29 | +50° ± 3° | 0.74 | 1N.HCl |
| 23 | H | $(C_2H_5)_2NCH_2CH_2-$ | H | H | 194–79 | −20° ± 2° | 0.97 | EtOH |
| 24 | $CH_2=CH-CH_2$ | $CH_2=CH-CH_2-$ | H | H | 224–27 | −50° ± 3° | 0.8 | 1N.HCl |
| 25 | H | $(CH_3)_2NCH_2CH_2-$ | H | H | 165–67 | −44° ± 2° | 0.8 | $H_2O$ |
| 26 | H | $CH_2=C(CH_3)-CH_2-$ | H | H | 198–200 | −10° ± 1° | 1.0 | 1N.HCl |
| 27 | H | $CH_3-CH(OH)-CH_2-$ | H | H | 188 dec | −42° ± 2° | 0.6 | $H_2O$ |
| 28 | H | 2,3-dimethoxyphenyl-$CH_2CH_2-$ | | | 104–106 | −40° ± 3° | 1.2 | $H_2O$ |
| 29 | H | cyclopropyl | $CH_3CO-$ | $CH_3CO-$ | 78–87 | −17.3° ± 2° | 0.58 | EtOH |
| 30 | H | cyclopropyl-$CH_2-$ | H | H | 216–18 | −17.7° ± 2° | 0.56 | 1N.HCl |

-continued

| | | | | | | | | |
|---|---|---|---|---|---|---|---|---|
| 31 | H | $CH_3CH_2-$ | $\underset{CH_3C-}{\overset{O}{\underset{\|}{\|}}}$ $\underset{CH_3C-}{\overset{O}{\underset{\|}{\|}}}$ | | 96–102 | $-19° \pm 2°$ | 1.8 | $H_2O$ |
| 32 | H | $CH_2=CH-CH_2-$ | isopropylidene | | 214–16 | $-3.6° \pm 0.8°$ | 1.4 | 1N.HCl |
| 33 | H | $CH_3CH_2-$ | isopropylidene | | 225–29 | $-22° \pm 2°$ | 0.89 | 1N.HCl |
| 34 | H |  | isopropylidene | | 185–87 | $-5° \pm 1°$ | 1.0 | EtOH |

| Examples Contd. | $R_f(1)$ | Empirical Formulae and Microanalysis |
|---|---|---|
| 18 | 0.62 | $C_{18}H_{26}N_6O_4 \cdot 3H_2O$ |
| | | Calcd. C, 49.31; H, 5.97; N, 19.17; 0, - |
| | | Found. C, 49,73; H, 4.29; N, 19.45; 0, - |
| 19 | 0.61 | $C_{20}H_{27}N_6O_4$ |
| | | Calcd. C, 57.82; H, 6.55; N, 20.23; 0, 15.40 |
| | | Found. C, 57.51; H, 6.42; N, 20.01; 0, 15.80 |
| 20 | 0.57 | $C_{17}H_{19}N_7O_4 \cdot H_2O$ |
| | | Calcd. C, 50.62; H, 5.24; N, 24.30; 0, 19.82 |
| | | Found. C, 50.96; H, 4.56; N, 23.41; 0, 19.19 |
| 21 | 0.32 | $C_{12}H_{16}N_6O_5$ |
| | | Calcd. C, 44.44; H, 4.97; N, 25.91; 0, 24.67 |
| | | Found. C, 44.64; H, 5.14; N, 25.55; 0, 24.70 |
| 22 | 0.62 | $C_{18}H_{20}N_6O_5 1/2H_2O$ |
| | | Calcd. C, 52.81; H, 5.17; N, 20.53; 0, 21.49 |
| | | Found. C, 52.21; H, 4.90; N, 20.38; 0, 20.72 |
| 23 | — | $C_{16}H_{25}N_7O_4$ |
| | | Calcd. C, 50.65; H, 6.64; N, 25.84; 0, - |
| | | Found. C, 50.97; H, 6.81; N, 25.93; 0, - |
| 24 | 0.62 | $C_{16}H_{20}N_6O_4$ |
| | | Calcd. C, 53.33; H, 5.59; N, 23.32; 0, - |
| | | Found. C, 53.25; H, 5.77; N, 27.18; 0, - |
| 25 | — | $C_{14}H_{21}N_7O_4$ |
| | | Calcd. C, 47.86; H, 6.02; N, 27.90; 0, - |
| | | Found. C, 47.68; H, 6.01; N, 27.91; 0, - |
| 26 | 0.59 | $C_{14}H_{18}N_6O_4$ |
| | | Calcd. C, 50.30; H, 5.39; N, 25.15; 0, 19.16 |
| | | Found. C, 50.50; H, 5.62; N, 24.97; 0, 19.46 |
| 27 | 0.43 | $C_{13}H_{18}N_6O_5(2)$ |
| 28 | 0.35 | $C_{20}H_{24}N_6O_6(2)$ |
| 29 | 0.51 | $C_{17}H_{20}N_6O_6$ |
| | | Calcd. C, 50.49; H, 4.99; N, - ; 0, - |
| | | Found. C, 50.38; H, 5.16; N, - ; 0, - |
| 30 | — | $C_{14}H_{18}N_6O_4 \cdot EtOH$ |
| | | Calcd. C, 50.52; H, 6.36; N, 22.09; 0, 21.03 |
| | | Found. C, 49.80; H, 6.32; N, 23.18; 0, 21.03 |
| 31 | — | $C_{16}H_{20}N_6O_6$ |
| | | Calcd. C, 48.98; H, 5.14; N, - ; 0, 24.47 |
| | | Found. C, 47.96; H, 5.19; N, - ; 0, 24.58 |
| 32 | — | $C_{16}H_{20}N_6O_4$ |
| | | Calcd. C, 53.33; H, 5.59; N, 23.32; 0, - |
| | | Found. C, 53.53; H, 5.68; N, 23.39; 0, - |
| 33 | 0.66 (3) | $C_{15}H_{20}N_6O_4$ |
| | | Calcd. C, 51.72; H, 5.79; N, 24.12; 0, - |
| | | Found, C, 51.74; H, 5.82; N, 24.47; 0, - |
| 34 | — | $C_{16}H_{20}N_6O_4$ |
| | | Calcd. C, 53.33; H, 5.59; N, 23.32; 0, - |
| | | Found. C, 53.39; H, 5.48; N, 23.43; 0, - |

(1)$R_f$ values are obtained from the TLC. Unless otherwise specified, solvent system used was; nBuOH:NH$_4$OH:H$_2$O: 86:5:14. All compounds had a single spot in the TLC
(2)The total of the percentage composition of all the elements (C, H, N & O) determined by the analyst was only 95% or less. The compounds had a single spot in the TLC. Their structures were followed by the infrared spectra and confirmed by the nmr.
(3)Solvent system: n-Butanol saturated with water.

While all of the compounds of this invention exhibit cardiovascular activity, only certain of the compounds exhibit anti-inflammatory activity. The following table summarizes the anti-inflammatory activity in the rat paw edema assay:

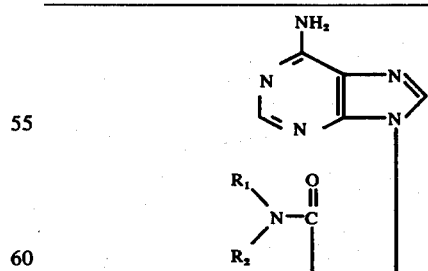

| $R_1$ | $R_3$ | $R_4$ | $ED_{25}$(mg./kg.) |
|---|---|---|---|
| $-C_2H_5$ | H | H | 0.137 |
| $-CH_2-CH=CH_2$ | H | H | 50 |

-continued

| $R_1$ | $R_3$ | $R_4$ | $ED_{25}$(mg./kg.) |
|---|---|---|---|
| ◁ | H | H | 1.28 |
| —CH₂—C(CH₃)=CH₂ | H | H | 55 |
| —CH₂—CH(OH)—CH₃ | H | H | 75 |
| ◁ | acetyl | acetyl | 1.3 |

$R_2$ is H in each of the above compounds

The compounds of this invention can be formulated into various pharmaceutically acceptable dosage forms such as tablets, capsules, pills and the like for immediate or sustained releases by combining the active compound with suitable pharmaceutically acceptable carriers or diluents according to methods well-known in the art. Such dosage forms may automatically include excipients, binders, fillers, flavoring and sweetening agents and other therapeutically inert ingredients necessary in the formation of the desired preparation.

Preparations for parenteral administration include sterile, aqueous or non-aqueous solutions, suspensions or emulsions which are well-known in the art.

We claim:

1. A compound of the formula

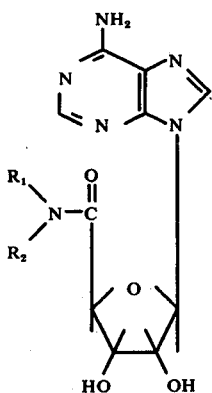

wherein $R_1$ is hydrogen and $R_2$ is phenyl, loweralkylphenyl, substituted phenyl, adamantyl, 2-methylfufuryl, benzylamino or $R_1$ and $R_2$ taken together form a 5 or 6 membered heterocyclic moiety.

2. A compound of claim 1 wherein $R_1$ and $R_2$ taken together form a 5 or 6 membered heterocyclic moiety.
3. Adenosine-5'-[(N-allyl)carboxamide].
4. Adenosine-5'-[(N-ethoxyethyl)carboxamide].
5. Adenosine-5'-[(N-2-propynyl)carboxamide].
6. Adenosine-5'-[(N-2-methylfufuryl)carboxamide].
7. Adenosine-5'-(N-phenethyl)carboxamide.
8. Adenosine-5'-(N-adamantyl)carboxamide.
9. Adenosine-5'-(N-benzylamino)carboxamide.
10. Adenosine-5'-(N-ethoxyphenyl)carboxamine.
11. Adenosine-5'(N,N-diallyl)carboxamide.
12. Adenosine-5'-(N-2-methallyl)carboxamide.
13. Adenosine-5'-[N-(3,4-dimethoxyphenethyl)carboxamide].
14. Adenosine-5'-[N-(cyclopropylmethyl)carboxamide].
15. Adenosine-2',3'-diacetyl-5'-(N-cyclopropyl)carboxamide.
16. Adenosine-2',3'-diacetyl-5'-(N-ethyl)carboxamide.
17. A compound represented by the formula

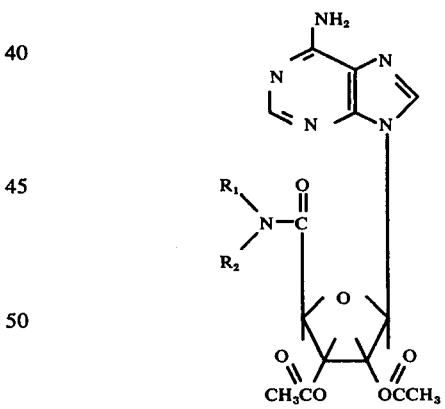

wherein $R_1$ is hydrogen and $R_2$ is phenyl, loweralkylphenyl, substituted phenyl, adamantyl, 2-methylfufuryl, benzylamino or $R_1$ and $R_2$ taken together form a 5 or 6 membered heterocyclic moiety.

* * * * *

UNITED STATES PATENT AND TRADEMARK OFFICE
CERTIFICATE OF CORRECTION

PATENT NO. : 4,029,884
DATED : June 14, 1977
INVENTOR(S) : H. H. Stein, et al.

It is certified that error appears in the above-identified patent and that said Letters Patent are hereby corrected as shown below:

In column 12, line 21, Claim 11, "diallyl" should read "dialkyl".

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*